(12) United States Patent
Ten Kate et al.

(10) Patent No.: US 9,006,498 B2
(45) Date of Patent: Apr. 14, 2015

(54) PROCESS FOR THE CHLORINATION OF A HYDROXYLATED ORGANIC COMPOUND

(75) Inventors: Antoon Jacob Berend Ten Kate, Arnhem (NL); André Michiel Koolaard, Zwolle (NL); Eilertdina Henderika Renkema, Renkum (NL); Carolina Anna Maria Christina Dirix, Diepenveen (NL); Luc Louis Théophile Vertommen, Westervoort (NL)

(73) Assignee: Akzo Nobel Chemicals International B.V., Amersfoort (NL)

( * ) Notice: Subject to any disclaimer, the term of this patent is extended or adjusted under 35 U.S.C. 154(b) by 0 days.

(21) Appl. No.: 14/241,570

(22) PCT Filed: Sep. 6, 2012

(86) PCT No.: PCT/EP2012/067354
§ 371 (c)(1),
(2), (4) Date: Feb. 27, 2014

(87) PCT Pub. No.: WO2013/034612
PCT Pub. Date: Mar. 14, 2013

(65) Prior Publication Data
US 2014/0371492 A1 Dec. 18, 2014

Related U.S. Application Data

(60) Provisional application No. 61/537,329, filed on Sep. 21, 2011.

(30) Foreign Application Priority Data

Sep. 9, 2011 (EP) ..................................... 11180744

(51) Int. Cl.
C07C 31/04 (2006.01)
C07C 31/18 (2006.01)
C07C 29/62 (2006.01)

(52) U.S. Cl.
CPC ..................................... C07C 29/62 (2013.01)

(58) Field of Classification Search
USPC .......................................... 568/841, 844, 852
See application file for complete search history.

(56) References Cited

U.S. PATENT DOCUMENTS 7,473,809 B2 * 1/2009 Kubicek et al. ............... 568/841

FOREIGN PATENT DOCUMENTS

| DE | 1075103 | 2/1960 |
|---|---|---|
| DE | 4032450 | 4/1991 |
| GB | 486 453 | 6/1938 |
| JP | 2010 047492 | 3/2010 |
| WO | WO 2005/021476 | 3/2005 |
| WO | WO 2005/054167 | 6/2005 |
| WO | WO 2006/020234 | 2/2006 |
| WO | WO 2008/074733 | 12/2007 |
| WO | WO 2008/074733 A1 * | 6/2008 |
| WO | WO 2008/110588 | 9/2008 |
| WO | WO 2009/016149 | 5/2009 |
| WO | WO 2010/106085 | 3/2010 |
| WO | WO 2011/000896 | 1/2011 |

OTHER PUBLICATIONS

International Search Report and Written Opinion for International Application No. PCT/EP2012/067354 dated Oct. 1, 2012.
C.H. Rochester, Acidity Functions, Academic Press, New York, 1970, Chapter 2.
Kirk-Othmer Encyclopedia of Chemical Technology, Third Edition, vol. 9, John Wiley & Sons, 1980, pp. 432-471.
Wurtz, A. (1859) Compt. Rend. 48: 101-104, cited and described in specification, see WO2013/034612, p. 13, lines 11-15.
P.P. McClellan, "Manufacture and Uses of Ethylene Oxide and Ethylene Glycol", 1950, Ind. Eng. Chem. 42: 2404-2407.
Organic Syntheses, Coll. vol. 8, p. 434 (1993).
Kirk-Othmer Encyclopedia of Chemical Technology, Third Edition, vol. 19, John Wiley & Sons (1982), pp. 246-274.
International Preliminary Report on Patentability for International Application No. PCT/EP2012/067354 dated Mar. 12, 2014.

* cited by examiner

Primary Examiner — Jafar Parsa
(74) Attorney, Agent, or Firm — Kenyon & Kenyon LLP

(57) ABSTRACT

Process for the chlorination of an organic compound comprising at least one aliphatic hydroxyl group, said process comprising the steps of actively adding to said organic compound (i) hydrogen chloride and (ii) a HCl desolubilizer or a precursor thereof, and heating the resulting mixture at a reaction temperature in the range 20°-160° C., wherein said chlorination is performed in the presence of a catalyst selected from the group consisting of (a) ketones, (b) aldehydes, (c) carboxylic acids with 1-8 carbon atoms, (d) organic compounds comprising a β-diketone moiety or a β-keto aldehyde moiety, and (e) organic polymers comprising at least one carbonyl group, having a vapor pressure at the reaction temperature of less than 1 mbar, a weight average molecular weight $M_w$ of 500 g/mole or more, and are soluble in the reaction mixture at the reaction temperature, and wherein the HCl desolubilizer is an alkali metal chloride salt, an alkaline earth metal chloride salt, or an acid.

20 Claims, 2 Drawing Sheets

PROCESS FOR THE CHLORINATION OF A HYDROXYLATED ORGANIC COMPOUND

The present invention relates to a process for the chlorination of an organic compound comprising at least one aliphatic hydroxyl group by hydrogen chloride.

This process is industrially relevant because the resulting products can be used in the preparation of epoxides. Epichlorohydrin, for example, which is a widely used precursor for epoxy resins, can be prepared by reacting a dichloropropanol such as 2,3-dichloropropan-1-ol or 1,3-dichloropropan-2-ol with a base.

Known processes to prepare dichloropropanol include the chlorination of glycerol using anhydrous hydrochloric acid. This process is described in many publications, using various catalysts. For instance, WO 2005/021476 discloses the use of organic acids as catalysts; WO 2010/106085 discloses the use of ketone or aldehyde catalysts; WO 2008/074733 discloses polymeric catalysts.

The disadvantage of these processes is that part of the fed hydrogen chloride remains unreacted in the final reaction mixture.

Furthermore, in a subsequent purification step, the presence of dissolved HCl makes it difficult to separate the formed dichloropropanol from the formed water. HCl works as a solubilizer for the system of dichloropropanol and water. At sufficient concentration it can even completely eliminate the immiscibility gap that the binary system of dichloropropanol and water exhibits, thus impeding separation by methods based on liquid-liquid split, such as decanting, which typically are energy efficient separation methods. But also distillation is hampered by the strong interaction of HCl, dichloropropanol, and water. So, either difficult separation schemes have to be set up to separate dichloropropanol, water, and HCl (see e.g. WO 2011/000896) or HCl has to be neutralized, e.g. with NaOH, which not only calls for alkaline usage but also leads to salt waste.

A first object of the present invention is therefore to provide a process for the chlorination of a hydroxyl-functional organic compound in which the amount of unreacted hydrogen chloride in the reaction mixture is minimized. At the same time, it is an object to reduce the amount of NaOH required for neutralizing the reaction mixture and, consequently, to reduce salt waste streams.

The reaction between glycerol and hydrogen chloride not only leads to dichloropropanols (2,3-dichloropropan-1-ol and 1,3-dichloropropan-2-ol) but also to monochloropropanol (3-chloropropane-1,2-diol and 2-chloropropane-1,3-diol; also called monochlorohydrin; MCH). In view of the above, it will be evident that there is a desire to improve the selectivity of the reaction towards dichloropropanol (also called dichlorohydrin; DCH).

A further object of the present invention is therefore to provide a process with an improved selectivity for dichlorinated compounds compared to monochlorinated ones.

It has surprisingly been found that these objects can be met by actively adding to the reaction mixture a HCl desolubilizer, which is an acid, an alkali chloride salt, or alkaline earth chloride salt that is able to reduce the solubility of HCl in the reaction mixture according to the test described below.

This is indeed surprising, because it is generally desired to have the highest possible HCl concentration in the reaction mixture; having a HCl desolubilizer present during the reaction would be considered unfavourable. Without wanting to be limited to theory, one explanation could be found in that part of the hydrogen chloride dissolved in the water formed during the reaction becomes dissociated. This dissociated hydrogen chloride is not or only very slowly reactive towards glycerol and its derivatives. Hence, part of the added hydrogen chloride is deactivated during the process.

The following test determines whether or not a substance is a HCl desolubilizer. This test is conducted in a thermostated glass autoclave equipped with a pressure gauge with a total system volume of one liter. The test procedure consists of two parts.

In the first part, the test unit is thermostated at 25° C. and then evacuated at 100 mbar or below. This pressure is recorded as "the evacuation pressure". Then, 450 ml of an aqueous solution of 34 wt % hydrogen chloride are injected into the test unit. After equilibration, the system pressure is recorded as "the reference pressure". The reference pressure will be approximately 270 mbar at an evacuation pressure of 100 mbar.

In the second part, the test unit is thermostated at 25° C. and filled with 100 grams of the test substance. Subsequently it is evacuated at the same evacuation pressure as used during the first part of the test. Next, 345 ml of the aqueous solution of 34 wt % hydrogen chloride are injected into the test unit. After equilibration the system pressure is recorded as "the recorded pressure". The test substance is characterized as HCl desolubilizer when this recorded pressure is higher than the reference pressure as observed in the first part of the test.

The quality of the test substance as HCl desolubilizer can be quantified by the ratio of the recorded pressure divided by the reference pressure. If this ratio is only slightly above 1, the test substance is a weak HCl desolubilizer; if this ratio is 2 or more, the test substance is defined as a strong HCl desolubilizer. Hence, in a preferred embodiment, a HCl desolubilizer with a ratio of the recorded pressure divided by the reference pressure of at least 2 is used in the process of the invention.

The present invention therefore relates to a process for the chlorination of an organic compound comprising at least one aliphatic hydroxyl group which comprises the steps of actively adding to said organic compound (i) hydrogen chloride and (ii) a HCl desolubilizer or a precursor thereof, and heating the resulting mixture at a reaction temperature in the range 20°-160° C. The HCl desolubilizer is an alkali metal chloride salt, an alkaline earth metal chloride salt, or an acid. The chlorination is performed in the presence of a catalyst selected from the group consisting of (a) ketones, (b) aldehydes, (c) carboxylic acids with 1-8 carbon atoms, (d) organic compounds comprising a β-diketone moiety or a β-keto aldehyde moiety, and (e) organic polymers comprising at least one carbonyl group, having a vapour pressure at the reaction temperature of less than 1 mbar, a weight average molecular weight $M_w$ of 500 g/mole or more, and are soluble in the reaction mixture at the reaction temperature.

In the process of the present invention, both the HCl desolubilizer or its precursor and the hydrogen chloride are actively added to the reaction mixture, which means that the hydrogen chloride is not solely formed in-situ and the HCl desolubilizer is present during the actual chlorination reaction.

This active addition of hydrogen chloride thus differs from the manner in which HCl is introduced in the process of WO 2005/054167, which involved an in-situ generation of HCl by reaction of an inorganic acid such as sulfuric or phosphoric acid with a metal chloride salt.

The process according to the invention also differs from that of WO 2008/110588, which involved the addition of a "salt-out salt" to the reaction mixture after the reaction between glycerol and HCl had been completed, in order to reduce the amount of HCl dissolved in the reaction medium in the course of a separation step. So, in contrast to the present invention, said document discloses the addition of a metal salt after the reaction, while the present process requires the HCl desolubilizer to be present during the reaction of HCl and the organic compound.

The presence of a salt during the reaction is neither disclosed nor suggested in this document.

Furthermore, it has been found that the preferred salt according to this document, NaCl, is not able to reduce the loss of hydrogen chloride in the process according to the present invention.

Organic compounds suitable for chlorination using the process according to the present invention are liquid at the reaction temperature and comprise at least one, preferably at least two aliphatic hydroxyl groups. The term "aliphatic hydroxyl group" refers to a carbon atom bearing only one—not more—hydroxyl (OH) functionality. This hydroxyl-functionalized carbon atom is preferably sp3 hybridized. The OH groups can be primary, secondary, or tertiary OH functionalities. Besides the one or more aliphatic hydroxyl groups, the organic compound which is to be chlorinated may contain other heteroatoms such as a halides, sulfur, phosphorus, nitrogen, oxygen, silicon, boron, or combinations thereof. The organic compound comprising at least one aliphatic hydroxyl group preferably is a $C_2$-$C_{40}$, preferably $C_3$-$C_{15}$, hydrocarbon, linear or branched, preferably comprising at least one primary hydroxyl group.

More specific examples of organic compounds which are suitable for being chlorinated according to the process of the present invention include mono-alcohols, including ethanol, propanol, butanol, pentanol, isoamyl alcohol, hexanol, heptanol, octanol, nonanol, decanol, undecanol, and dodecanol, and polyols—i.e. organic compounds with at least two aliphatic hydroxyl groups—including 1,2-ethanediol, 1,2-propanediol, 1,3-propanediol, 1,4-butanediol, 1,3-butanediol, 1,2,4-butanetriol, 1,5-pentanediol, 1,2-pentanediol, isopentanediol, 1,6-hexanediol, 1,2-hexanediol, 1,3-hexanediol, 1,7-heptanediol, 1,8-octanediol, 1,9-nonanediol, 1,10-decanediol, 1,11-undecanediol, 1,12-dodecanediol, glycerol, ethylene glycol monoacetate, propanediol monoacetates, glycerin monoacetates, and glycerin monostearates.

In a particularly preferred embodiment of the present invention, glycerol (1,2,3,-propanetriol) is used as the organic compound which is to be chlorinated. In this case, preferably, glycerol is used which has been obtained as a byproduct in the production of biodiesel or during conversions of fats or oils of plant or animal origin in general, such as saponification, trans-esterification or hydrolysis reactions. Chlorinated products produced from glycerol, i.e. dichlorohydrins, are preferably used in conventional processes to produce epichlorohydrin in the presence of a base. The preparation of epichlorohydrin can take place as described for example in *Organic Syntheses, Coll.* Vol. 2, p. 256, Vol. 16, pages 30-31 or in DE 1 075 103.

Any monochlorohydrin that might be produced in the process of the invention can be used to prepare glycidol by bringing it into contact with a base. Such a process is described for example in WO 2009/016149.

It is noted that the present invention can also be applied for the chlorination of carbohydrates, i.e. monosaccharides (e.g. glucose), oligosaccharides (e.g. sucrose), and polysaccharides (e.g. cellulose, carboxymethylcellulose). The thus obtained products can be used as intermediates for the production of (fine) chemicals.

It may be preferred to purify the organic compound which is to be chlorinated before it is employed in the chlorination reaction by removing contaminants, e.g. water, organic contaminations or inorganic contaminations, before use. The purification can be performed using purification techniques well known in the art, such as distillation, extraction, absorption, centrifugation, or other appropriate methods.

The HCl desolubilizer is selected from alkali metal chloride salts, alkaline earth metal chloride salts, and acids that qualify as HCl desolubilizers according to the above-described test. Suitable chloride salts have a high solubility in water. Preferably, the chloride salts have such a high solubility that the relative chloride ion concentration in a saturated aqueous solution of said chloride salt is higher than the relative chloride concentration in an azeotropic composition of hydrochloric acid at atmospheric pressure. The relative chloride concentration is defined as the true molar chloride fraction divided by the true molar water fraction in the solution of concern. The relative chloride concentration in an azeotropic composition of hydrochloric acid at atmospheric pressure is 0.144. More specific examples of suitable chloride salts are the chloride salts of calcium, magnesium, beryllium, lithium, and caesium. More preferred salts are calcium chloride, lithium chloride, and magnesium chloride. For these salts, the relative chloride concentrations in saturated aqueous solutions are 0.269, 0.360, and 0.208 respectively.

Calcium chloride is the most preferred salt to be used.

Instead of adding these salts to the reaction mixture, it is also possible to add a precursor of these salts to the reaction mixture, i.e. compounds that form said salts in situ in the reaction mixture. Examples of suitable precursors are the oxides or hydroxides of the above-mentioned alkali and alkaline earth metals.

Acids qualify as HCl desolubilizers if they qualify as such according to the above-described test. Suitable acids are generally strong acids with a Hammett acidity function—at 25° C. and in their pure state (meaning: at least 99% pure)—lower than or equal to −7.5, preferably lower than or equal to −10, most preferably lower than or equal to −12.

The Hammett acidity function ($H_0$) is a measure for the acidity of strong acids, including super acids, and is defined as: $H_0 = pK_{BH+} + \log([B]/[BH^+])$ wherein $pK_{BH+}$ is $-\log(K)$ for the dissociation of $BH^+$, which is the conjugate acid of a very weak base B. More information about the Hammett acidity function can be obtained from C. H Rochester, *Acidity Functions*, Academic Press 1970, Chapter 2.

Examples of suitable acids are common strong acids like hydroiodic acid, hydrofluoric acid, hydrobromic acid, perchloric acid, sulfuric acid, methanesulfonic acid, and p-toluenesulfonic acid, and extremely strong acids like fluoroantimonic acid ($H[SbF_6]$), magic acid ($FSO_3HSbF_5$), carborane superacid ($H(CHB_{11}Cl_{11})$), fluorosulfuric acid ($FSO_3H$), and triflic acid ($CF_3SO_3H$).

The most preferred acid is sulfuric acid ($H_0$=−12). Because of their reactivity with the organic compound and their volatility, hydroiodic, hydrofluoric, and hydrobromic acid are the least preferred.

The HCl desolubilizer is preferably added to the reaction mixture in an amount of at least about 0.1 wt %, more preferably at least 1 wt %, most preferably at least 5 wt %, based on the weight of the liquid reaction mixture. The amount of HCl desolubilizer is preferably not more than 50 wt %, more preferably not more than 40 wt %, and most preferably not more than 25 wt %, based on the weight of the liquid reaction mixture.

The hydrogen chloride can be added in the form of an aqueous solution or as gaseous hydrogen chloride. The use of gaseous hydrogen chloride is most preferred. Although the application of pure hydrochloric acid (>99% pure) is preferred, a person skilled in the art will realize that the process according to the present invention is particularly suitable for application of raw materials with only limited purity, e.g. HCl produced as a byproduct of a chemical production process.

The chlorination is performed in the presence of a catalyst. The catalyst is selected from (a) ketones, such as acetone, methyl ethyl ketone (MEK), and acetophenone, (b) aldehydes, such as propionic aldehyde, (c) carboxylic acids with 1-8 carbon atoms, such as acetic acid, formic acid, propionic acid, butyric acid, valeric acid, caproic acid, heptanoic acid, octanoic acid, aromatic carboxylic acids such as benzoic acid, salycylic acid, 4-chlorobenzoic acid, 1,4-dichlorobenzoic acid, 4-nitrobenzoic acid, and 2,4-dinitrobenzoic acid, poly(carboxylic acids) such as dicarboxylic acids like succinic acid, glutaric acid, adipic acid, and octanedioic acid (suberic acid) and tri- and tetracarboxylic acids; (d) organic compounds comprising a β-diketone moiety or a β-keto aldehyde moiety, and (e) organic polymers comprising at least one carbonyl group, having a vapour pressure at the reaction temperature of less than 1 mbar, a weight average molecular weight $M_w$ of 500 g/mole or more, and are soluble in the reaction mixture at the reaction temperature. These organic polymers are disclosed in WO 2008/074733. Examples of such polymers are polyester amide hyper-branched polymers, polyacrylamide, and polyacrylic acid.

Carboxylic acids with 1-8 carbon atoms are generally more active catalysts than larger acids.

Preferred catalysts are carboxylic acids and organic compounds comprising a β-diketone moiety or a β-keto aldehyde moiety. Examples of the latter compounds are 2,4-pentanedione (which is also denoted as acetylacetone), 1-phenyl-1,3-butanedione (also denoted as 1-benzoylacetone), dibenzoylmethane, 3,5-heptanedione, 1,3-cyclopentanedione, 2,4-hexanedione, 1,3-cyclohexanedione, triacetylmethane, 1,1,2-triacetylethane, 2,4,6-heptanetrione, 1,3,5- and cyclohexanetrione, and 1,1,2,2-tetraacetylethane.

More preferred catalysts are selected from the group consisting of acetic acid, suberic acid, 2,4-pentanedione, glutaric acid, adipic acid, or a combination thereof. The most preferred catalysts are glutaric acid and adipic acid because they are the most active catalysts.

The catalyst can be introduced into the reaction vessel neat, as a solution in one of the reactants, e.g. glycerol, in an appropriate organic solvent, or in the form of a precursor leading to in-situ catalyst formation.

Suitable organic solvents include alcohols and esters.

Examples of precursors for organic acids are their esters and anhydrides; examples of precursors for ketones are the corresponding ketals; examples of precursors for aldehydes are the corresponding acetals.

The addition of the catalyst can be performed continuously or discontinuously. The catalyst according to the present invention is typically used in an amount of at least 0.05% by weight, more preferably at least 0.5% by weight, and most preferably at least 1% by weight, based on the total weight of the liquid reaction mixture. Preferably, no more than 50% by weight, more preferably no more than 25% by weight, and most preferably no more than 15% by weight of catalyst is employed, based on the total weight of the liquid reaction mixture.

In one embodiment of the process according to the present invention, the organic compound comprising at least one aliphatic hydroxyl group, the catalyst, and the HCl desolubilizer or its precursor are placed in a closed reaction vessel, heated, and pressurized under an atmosphere of hydrogen chloride. The reaction mixture is heated to the desired temperature for the desired length of time. The reaction mixture is then discharged from the reaction vessel and either purified or sent to other equipment for further processing or to storage.

Alternatively, the organic compound comprising at least one aliphatic hydroxyl group is formed in-situ in the reaction mixture, for instance by hydrolysis. In that case, a hydrolysable precursor of said compound, for instance an ester, is added to the reaction mixture instead of said organic compound itself.

The present invention may include various process schemes. Thus, the process can be carried out in a batch reactor, preferably in fed-batch operation, or in a continuously operating system such as in a cascade of continuous flow reactors of the liquid gas type. Bubble columns are not preferred.

In an illustrative fed-batch process, one or more of the reagents are fed to a reaction vessel over a period of time throughout the reaction, while other reagents are fed only at the start of the reaction. In such a process, for example, the organic compound comprising at least one aliphatic hydroxyl group, the HCl desolubilizer or its precursor, and the catalyst may be fed in a single batch to a halogenation reactor, which is then held at reaction conditions for a suitable time, while hydrogen chloride gas is fed continuously through the reaction mixture at the desired rate, which may be at constant flow or constant pressure. After the reaction, the hydrogen chloride feed can be terminated, and the reactor contents can be discharged for storage, purification or further processing.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing. In such a scheme, the organic compound comprising at least one aliphatic hydroxyl group, the HCl desolubilizer or its precursor, and the catalyst may be fed to the equipment and hydrogen chloride gas is added as desired at a single point or at multiple points throughout the process equipment, which may include continuously stirred tank reactors, tubes, pipes or combinations thereof.

In a continuous recycle process, one or more of the unreacted starting material, reaction intermediates, hydrogen chloride, HCl desolubilizer (or its precursor, if not yet fully converted), or catalyst exiting from the process equipment are recycled back to a point earlier in the process. In this manner, raw material efficiencies are maximized and/or catalysts reused. Since catalysts are reused in such a process scheme, it may be desirable to employ the catalyst in a higher concentration than is the case in a single-pass process, where they are often discarded. This may result in faster reactions, or in smaller process equipment, which results in lower capital costs for the equipment employed.

The total mean residence time of the reaction mixture in the reactor typically is at least 1 minute, preferably at least 2 hours, and most preferably at least 4 hours. Typically, the total mean residence time is less than 24 hours, more preferably less than 18 hours, most preferably less than 12 hours.

International patent applications WO 2006/020234 and WO 2005/054167 show detailed examples of suitable equipment for carrying out the process according to the present invention.

The hydrogen chloride can be added through nozzles, perforated plates or pipes, microporous plates, and ejectors. Typically, for each mole of hydroxyl groups to be chlorinated, at least 1 mole, more preferably at least 1.1 moles, and even more preferably at least 1.2 moles of hydrogen chloride gas are added. Typically, no more than 200 moles, preferably no more than 100 moles, and most preferably no more than 50 moles of hydrogen chloride gas are added for each mole of hydroxyl groups to be chlorinated.

Recovery of the chlorinated product can be achieved in a variety of ways. It is preferably achieved by distillation or evaporation, preferably in a continuous fashion, either directly from the reaction vessel or from a separate piece of equipment such as a vaporizer or a distillation column. Alternatively, the chlorinated product can be isolated via liquid extraction, absorption or any other kind of separation method.

To achieve higher conversions, it might be advisable to remove at least part of the water produced during the reaction. This can for example be achieved via distillation under reduced pressure. For this purpose, use may be made of any conventionally employed device for distillation, such as evaporators of various constructions with or without a source of heat, rectification columns with various internals such as trays, structured packing, random packing, etc.

The process according to the present invention is typically carried out at a reaction temperature of at least 20° C., more preferably at least 40° C., even more preferably at least 60° C., and most preferably at least 80° C. The temperature is at most 160° C., more preferably at most 150° C., even more preferably at most 140° C. Most preferably, the process is carried out at or just below the boiling temperature of the reaction mixture.

The process is preferably carried out at a pressure of at least 0.1 bar, preferably at least 0.3 bar, more preferably at least 0.5 bar, and most preferably it is carried out at atmospheric pressure or a pressure of at least 1 bar. Preferably, the pressure is not higher than 100 bar, more preferably not higher than 40 bar, even more preferably not higher than 20 bar, and most preferably not higher than 5 bar.

In another embodiment according to the invention, 1,2 ethanediol is used as the organic compound which is chlorinated to produce chloroethanol. Ethylene oxide can be prepared by bringing the chloroethanol into contact with a base (see for example *Kirk-Othmer Encyclopedia of Chemical Technology*, Third Edition, Vol. 9, John Wiley & Sons (1980), pp. 432-471; Wurtz, A. (1859). *Compt. rend.* 48: 101-104; P. P. McClellan (1950). "Manufacture and Uses of Ethylene Oxide and Ethylene Glycol". *Ind. Eng. Chem.* 42: 2402-2407).

In yet another embodiment according to the invention, 1,2-propanediol is used as the organic compound which is chlorinated to produce chloropropanol. Typically, a mixture of 1-chloro-2-propanol and 2-chloro-1-propanol is obtained, with 1-chloro-2-propanol being the major part. Propylene oxide can be prepared by bringing the chloropropanol into contact with a base. Such a process is described for example in *Organic Syntheses, Coll.* Vol. 8, p. 434 (1993); Vol. 66, p. 160 (1988); and *Kirk-Othmer Encyclopedia of Chemical Technology*, Third Edition, Vol. 19, John Wiley & Sons (1982), pp. 246-274).

FIGURES

FIG. 1 illustrates the selectivity to dichloropropanol as a function of the glycerol conversion using different (amounts of) HCl desolubilizers, as described below in the Examples.

FIG. 2 displays the HCl mass fraction in the reaction mixture as a function of time with different (amounts of) HCl desolubilizers, as described below in the Examples.

EXAMPLES

Comparative Example A

A mixture of 471.7 g of glycerol and 25.04 g of suberic acid in a one-liter, double-walled reactor was stirred and heated to 100° C. using an oil bath. Gaseous HCl was bubbled through the reaction mixture by means of an inlet pipe having a glass frit at its bottom to facilitate distribution of the gas into small gas bubbles.

The conversion and selectivity were determined on the basis of the mass fractions of glycerol, monochlorohydrin (MCH), and dichlorohydrin (DCH) as measured by HPLC (with dichlorohydrin being the combined fractions of 1,3-dichloropropan-2-ol and 2,3-dichloropropan-1-ol, and with monochlorohydrin being the combined fractions of 3-monochlorohydrin and 2-monochlorohydrin). For the HPLC analysis a 300 mg sample was taken from each sample. Subsequently, 50 ml of demineralized water were added and the mixture was homogenized. This sample was analyzed using an Ion 300 Interaction column (300*7.8 mm) at 40° C. using sulfuric acid 0.02 N as the eluent (injection volume of 20 µl). The flow rate was 0.4 ml per minute. An IR detector was used. Observed retention times were 23.3 min for glycerol, 29.8 min for 3-chloro-1,2-propanediol, 49.2 min for 1,3-dichloro-2-propanol, and 55.6 min for 2,3-dichloro-1-propanol.

The HCl mass fraction was determined by titration of the chloride content.

For each mass fraction the amount of original glycerol units was determined, and the conversion was calculated as the amount of C3 units (i.e. a unit of three carbon atoms which is present in glycerol, MCH, and DCH) in the MCH and DCH fractions, divided by the amount of C3 units in all fractions: $\{[DCH]+[MCH]\}/\{[glycerol]+[DCH]+[MCH]\}$.

The DCH selectivity was defined as $[DCH]/\{[DCH]+[MCH]\}$.

The loss in HCl efficiency is assessed as the ratio of the molar amount of HCl dissolved in the reaction mixture divided by the total molequivalent amount of Cl units present in the reaction, being the HCl fraction and the Cl fraction bonded in the organic structures.

Comparative Example B

This Examples illustrates the effect of NaCl on the process as described in Comparative Example A.

In order to determine whether or not NaCl is a HCl desolubilizer according to the definition given above, the test described above is conducted. That is: a test unit of one liter total volume, consisting of a thermostrated glass autoclave equipped with a pressure gauge, is thermostrated at 25° C. and then evacuated at an "evacuation pressure" of 100 mbar. Then, 450 ml of an aqueous solution of 34 wt % hydrogen chloride are injected into the test unit. After equilibration, the system pressure is 275 mbar, recorded as "the reference pressure".

After emptying and cleaning, the test unit is thermostated at 25° C. and filled with 100 grams of dry NaCl crystals. Subsequently it is evacuated at 100 mbar. Next, 345 ml of the aqueous solution of 34 wt % hydrogen chloride are injected into the test unit. After equilibration the system pressure is 259 mbar, recorded as "the recorded pressure".

Since the recorded pressure is not higher than the reference pressure, NaCl is not characterized as HCl desolubilizer.

Furthermore, the relative chloride concentration in a saturated aqueous NaCl solution is only 0.111, which is below the relative chloride concentration in an azeotropic composition of hydrochloric acid at atmospheric pressure (0.144).

A mixture of 471.8 g of glycerol (99.5% pure, ex J. T. Baker), 25.04 g of suberic acid, and 110.1 g of dry sodium chloride (NaCl) in a one-liter double-walled reactor was stirred and heated to 100° C. using an oil bath. Gaseous HCl was bubbled through the reaction mixture by means of an inlet pipe having a glass frit at its bottom to facilitate distribution of the gas into small gas bubbles. The HCl was added at a rate of 160 g per hour for 388 minutes. In total, 1,044 g of HCl were bubbled through the reaction mixture.

The HCl mass fraction was determined by acid/base titration.

Figure 1:
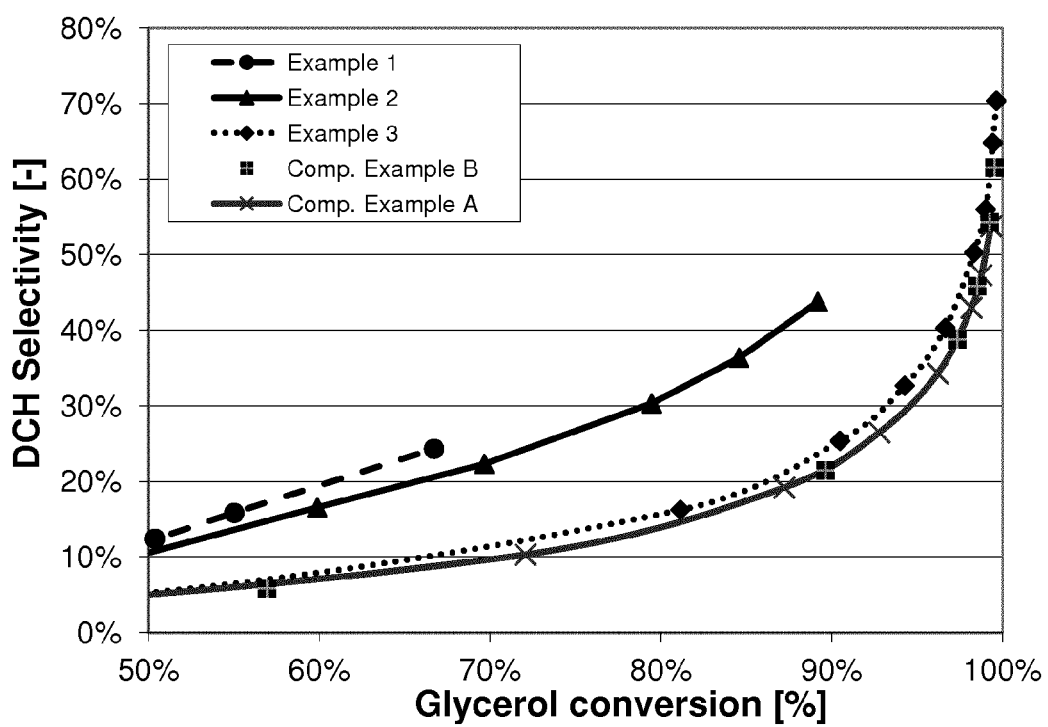
FIG. 1 shows the selectivity to DCH as a function of the glycerol conversion.
Figure 2:
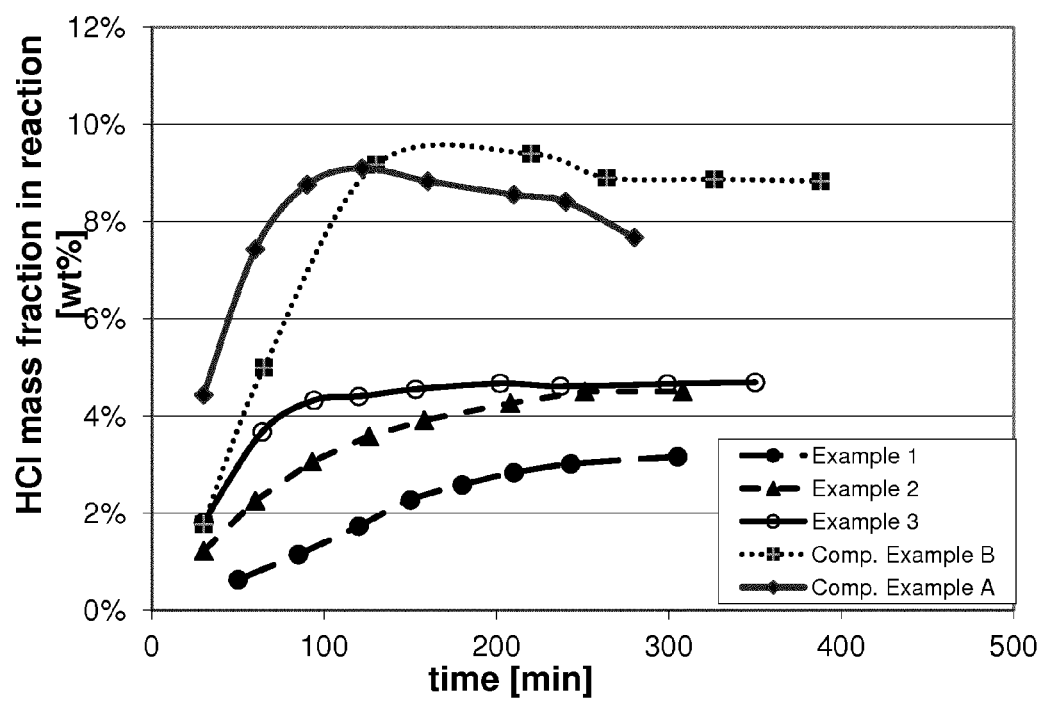
FIG. 2 shows the HCl mass fraction in the reaction mixture as a function of time. The loss in HCl efficiency is 18.3% at the end of the reaction.

Conversion, selectivity, and loss in HCl efficiency are displayed in FIG. 1 and FIG. 2.

The loss in HCl efficiency is 20.6% at the end of the reaction, which is even more than in Comparative Example 1, showing that the addition of NaCl certainly does not improve the efficiency of HCl usage.

It is furthermore clear that NaCl also does not improve the selectivity of the reaction.

Example 1

In order to determine whether or not $CaCl_2$ is a HCl desolubilizer according to the definition given above, the test described in Comparative Example B for NaCl is repeated with $CaCl_2$ instead of NaCl. The recorded pressure with $CaCl_2$ is 1080 mbar.

Since the recorded pressure is higher than the reference pressure, $CaCl_2$ is characterized as HCl desolubilizer. Actually, since the ratio of the recorded pressure divided by the reference pressure is 3.9, $CaCl_2$ is characterized as a strong HCl desolubilizer.

A mixture of 471.7 g of glycerol (99.5% pure, ex J. T. Baker) and 25.03 g of suberic acid and 125.3 g of dry calcium chloride ($CaCl_2$; 20.1 wt % in the reaction mixture) in a one-liter double-walled reactor was stirred and heated to 100° C. using an oil bath. Gaseous HCl was bubbled through the reaction mixture by means of an inlet pipe having a glass frit at its bottom to facilitate distribution of the gas into small gas bubbles. The HCl was added at a rate of 111 g per hour for 305 minutes. In total, 552 g of HCl were bubbled through the reaction mixture.

The HCl mass fraction was determined by acid/base titration.

Conversion, selectivity and loss in HCl efficiency are displayed in FIG. 1 and FIG. 2.

The loss in HCl efficiency is 14.3% at the end of the reaction, which is less than in Comparative Example 1, showing that the addition of $CaCl_2$ improves the efficiency of HCl usage.

Furthermore, $CaCl_2$ significantly improves the selectivity of the reaction.

Example 2

Example 1 was repeated with 17.4 wt % $CaCl_2$ in the reaction mixture.

Conversion, selectivity, and loss in HCl efficiency were determined as in Comparative Example A and are also displayed in FIG. 1 and FIG. 2.

The loss in HCl efficiency is 14.2% at the end of the reaction, which is less than in Comparative Example 1, showing that the addition of $CaCl_2$ improves the efficiency of HCl usage.

Example 3

In order to determine whether or not $H_2SO_4$ is a HCl desolubilizer according to the definition given above, the test described in Comparative Example B for NaCl is repeated with $H_2SO_4$ instead of NaCl. The recorded pressure with $H_2SO_4$ is 746 mbar.

Since the recorded pressure is more than twice the reference pressure, $H_2SO_4$ is characterized as strong HCl desolubilizer.

A mixture of 471.4 g of glycerol (99.5% pure, ex J. T. Baker) and 25.03 g of suberic acid and 110.3 g of sulfuric acid (96%) in a one-liter double-walled reactor was stirred and heated to 100° C. using an oil bath. Gaseous HCl was bubbled through the reaction mixture by means of an inlet pipe having a glass frit at its bottom to facilitate distribution of the gas into small gas bubbles. The HCl was added at a rate of 190 g per hour for 350 minutes. In total, 1,040 g of HCl were bubbled through the reaction mixture.

The HCl mass fraction was determined by titration of the chloride content.

Conversion, selectivity, and loss in HCl efficiency are displayed in FIG. 1 and FIG. 2.

The loss in HCl efficiency is 13.4% at the end of the reaction, which is less than in Comparative Example 1, showing that the addition of $H_2SO_4$ improves the efficiency of HCl usage.

Furthermore, sulfuric acid significantly improves the selectivity of the reaction compared to the Comparative Examples.

Example 4

In this Example, $MgCl_2$ and LiCl are tested for their HCl desolubilizing capabilities.

The test described in Comparative Example B for NaCl is repeated with $MgCl_2$ and with LiCl. The recorded pressure with $MgCl_2$ is 1830 mbar; the recorded pressure with LiCl is 1980 mbar.

Since the recorded pressures are more than twice the reference pressure, $MgCl_2$ and LiCl are both strong HCl desolubilizers.

The invention claimed is:

1. A process for the chlorination of an organic compound comprising at least one aliphatic hydroxyl group, said process comprising the steps of actively adding to said organic compound (i) hydrogen chloride and (ii) a HCl desolubilizer or a precursor thereof, and heating the resulting mixture at a reaction temperature in the range 20°-160° C., wherein said chlorination is performed in the presence of a catalyst selected from the group consisting of (a) ketones, (b) aldehydes, (c) carboxylic acids with 1-8 carbon atoms, (d) organic compounds comprising a β-diketone moiety or a β-keto aldehyde moiety, and (e) organic polymers comprising at least one carbonyl group, having a vapour pressure at the reaction temperature of less than 1 mbar, a weight average molecular weight $M_w$ of 500 g/mole or more, and are soluble in the reaction mixture at the reaction temperature, and wherein the HCl desolubilizer is an alkali metal chloride salt, an alkaline earth metal chloride salt, or an acid.

2. The process according to claim 1 wherein the HCl desolubilizer is a strong HCl desolubilizer.

3. The process according to claim 1 wherein the HCl desolubilizer is selected from the group consisting of calcium chloride, lithium chloride, magnesium chloride, beryllium chloride, and caesium chloride.

4. The process according to claim 3 wherein the HCl desolubilizer is selected from the group consisting of calcium chloride, lithium chloride, and magnesium chloride.

5. The process according to claim 4 wherein the HCl desolubilizer is calcium chloride.

6. The process according to claim 1 wherein the HCl desolubilizer is an acid having a Hammett acidity function at 25° C. and in its at least 99% pure state of −7.5 or less.

7. The process according to claim 6 wherein the acid is a strong acid or a super acid.

8. The process according to claim 7 wherein the acid is sulfuric acid.

9. The process according to claim 1 wherein the HCl desolubilizer is added to the organic compound in an amount of 0.1-50 wt %, based on the weight of the liquid reaction mixture.

10. The process according to claim 1 wherein the catalyst is selected from the group consisting of acetic acid, suberic acid, 2,4-pentadione, glutaric acid, adipic acid, and combinations thereof.

11. The process according to claim 1 wherein the organic compound comprising at least one aliphatic hydroxyl group is a $C_2$-$C_{40}$ hydrocarbon, linear or branched, comprising at least one hydroxyl group.

12. The process according to claim 1 wherein the organic compound comprises at least two aliphatic hydroxyl groups.

13. The process according to claim 11 wherein the organic compound comprising at least one aliphatic hydroxyl group is selected from the group consisting of ethanol, propanol, butanol, pentanol, isoamyl alcohol, hexanol, heptanol, octanol, nonanol, decanol, undecanol, dodecanol, 1,2-ethanediol, 1,2-propanediol, 1,3-propanediol, 1,4-butanediol, 1,3-butanediol, 1,2,4-butanetriol, 1,5-pentanediol, 1,2-pentanediol, isopentanediol, 1,6-hexanediol, 1,2-hexanediol, 1,3-hexanediol, 1,7-heptanediol, 1,8-octanediol, 1,9-nonanediol, 1,10-decanediol, 1,11-undecanediol, 1,12-dodecanediol, glycerol, ethylene glycol monoacetate, propanediol monoacetate, glycerin monoacetates, glycerin monostearates, and glycerin diacetates.

14. The process according to claim 13 wherein the organic compound comprising at least one aliphatic hydroxyl group is selected from the group consisting of glycerol, 1,2-ethanediol, 1,2-propanediol, and 1,3-propanediol.

15. The process according to claim 14 wherein the resulting halogenated product is used to prepare epichlorohydrin, by contacting it with a base.

16. The process according to claim 1 wherein the HCl desolubilizer is an acid having a Hammett acidity function at 25° C. and in its at least 99% pure state of −12 or less.

17. The process according to claim 3 wherein the HCl desolubilizer is added to the organic compound in an amount of 0.1-50 wt %, based on the weight of the liquid reaction mixture.

18. The process according to claim 9 wherein the catalyst is selected from the group consisting of acetic acid, suberic acid, 2,4-pentadione, glutaric acid, adipic acid, and combinations thereof.

19. The process according to claim 6 wherein the organic compound comprising at least one aliphatic hydroxyl group is a $C_2$-$C_{40}$ hydrocarbon, linear or branched, comprising at least one hydroxyl group.

20. The process according to claim 3 wherein the organic compound comprises at least two aliphatic hydroxyl groups.

* * * * *